United States Patent
Bjornberg

(10) Patent No.: US 6,868,623 B2
(45) Date of Patent: Mar. 22, 2005

(54) PROCESS FOR CONTROLLING THE TEMPERATURE OF A WEB AND A DEVICE TO USE FOR SAID TEMPERATURE CONTROL

(75) Inventor: Thomas Bjornberg, Vargon (SE)

(73) Assignee: Ircon Drying Systems AB (SE)

( * ) Notice: Subject to any disclaimer, the term of this patent is extended or adjusted under 35 U.S.C. 154(b) by 0 days.

(21) Appl. No.: 10/474,059

(22) PCT Filed: Apr. 26, 2002

(86) PCT No.: PCT/SE02/00826

§ 371 (c)(1),
(2), (4) Date: Oct. 6, 2003

(87) PCT Pub. No.: WO02/088462

PCT Pub. Date: Nov. 7, 2002

(65) Prior Publication Data

US 2004/0128856 A1 Jul. 8, 2004

(30) Foreign Application Priority Data

Apr. 26, 2001 (SE) .............................. 0101481

(51) Int. Cl.⁷ ................................. F26B 3/34
(52) U.S. Cl. ............................. 34/269; 34/273; 34/524
(58) Field of Search ..................... 34/524, 560, 561, 34/273, 269, 446; 162/198, 263; 356/429

(56) References Cited

U.S. PATENT DOCUMENTS

| | | | | |
|---|---|---|---|---|
| 4,119,481 A | * | 10/1978 | Beckley | .................... 156/273.3 |
| 4,514,913 A | | 5/1985 | Stephansen | |
| 5,010,659 A | | 4/1991 | Treleven | |
| 5,135,122 A | * | 8/1992 | Gross et al. | ................. 219/685 |
| 5,263,839 A | | 11/1993 | Robinson | |
| 5,377,428 A | | 1/1995 | Clark | |
| 5,966,835 A | * | 10/1999 | Bakalar | ........................ 34/267 |
| 6,560,893 B1 | * | 5/2003 | Bakalar | ........................ 34/110 |

* cited by examiner

Primary Examiner—Kenneth Rinehart
(74) Attorney, Agent, or Firm—Rolf Fasth; Fasth Law Offices

(57) ABSTRACT

The present invention relates to a process for controlling the temperature of a product in the form of a web (12) that is influenced by an IR ramp (9) for surface treatment of the web (12). With the help of a number of temperature sensors (26), the temperature of the web (12) is measured continuously within evenly distributed zones across and along its direction of movement (28), and the values obtained from the respective zone of the web (12) are transmitted to the respective drier modules (2) for the purpose of subjecting the aforementioned zones of the web to heat. The invention also relates to an arrangement with which the aforementioned process is executed.

10 Claims, 12 Drawing Sheets

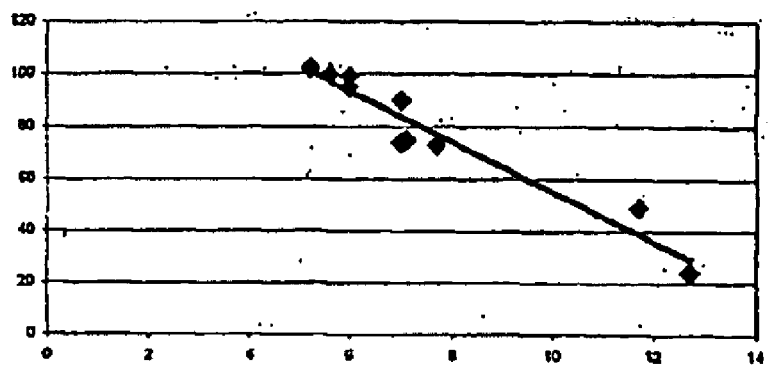
FIG.1
FIG.2
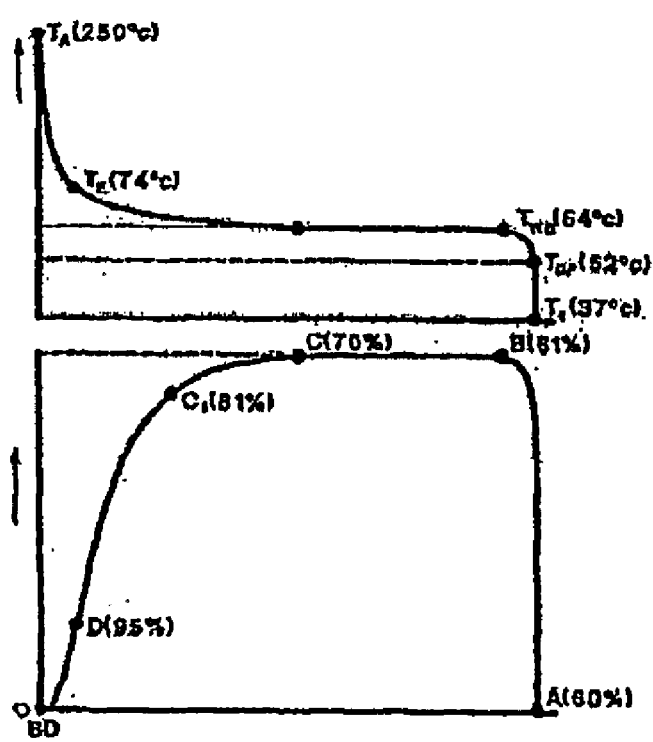

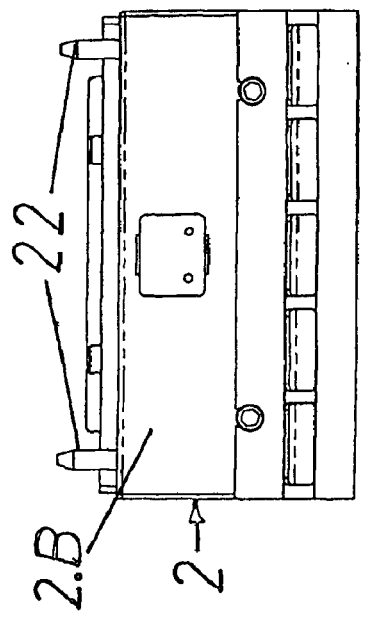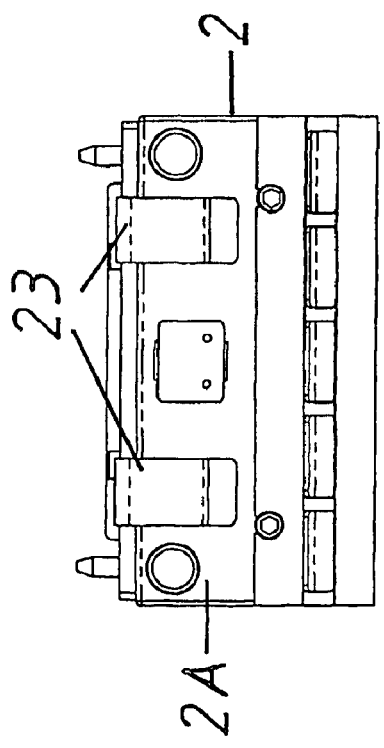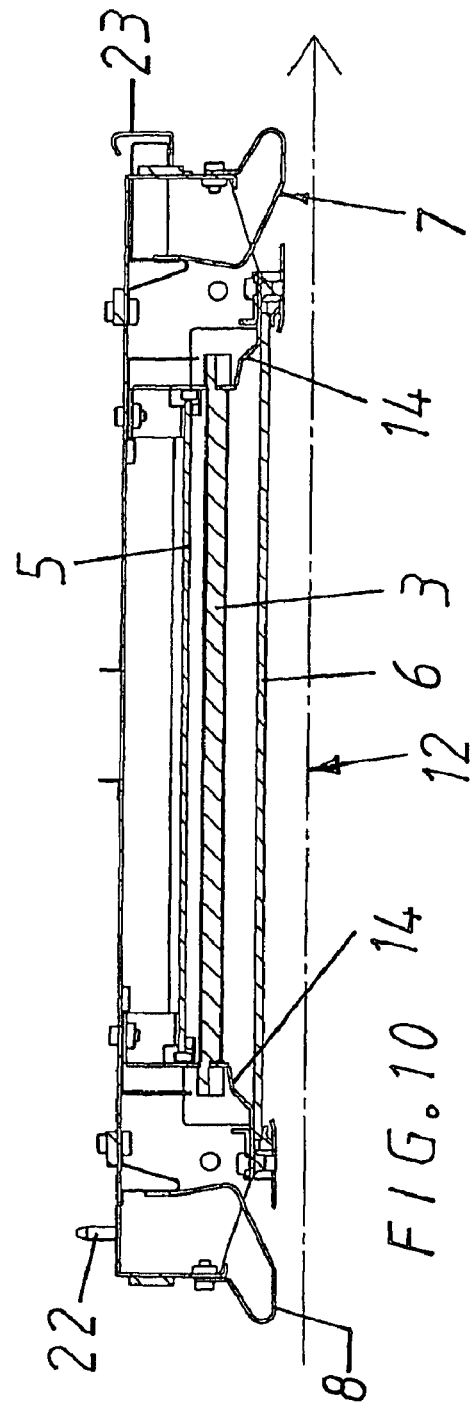

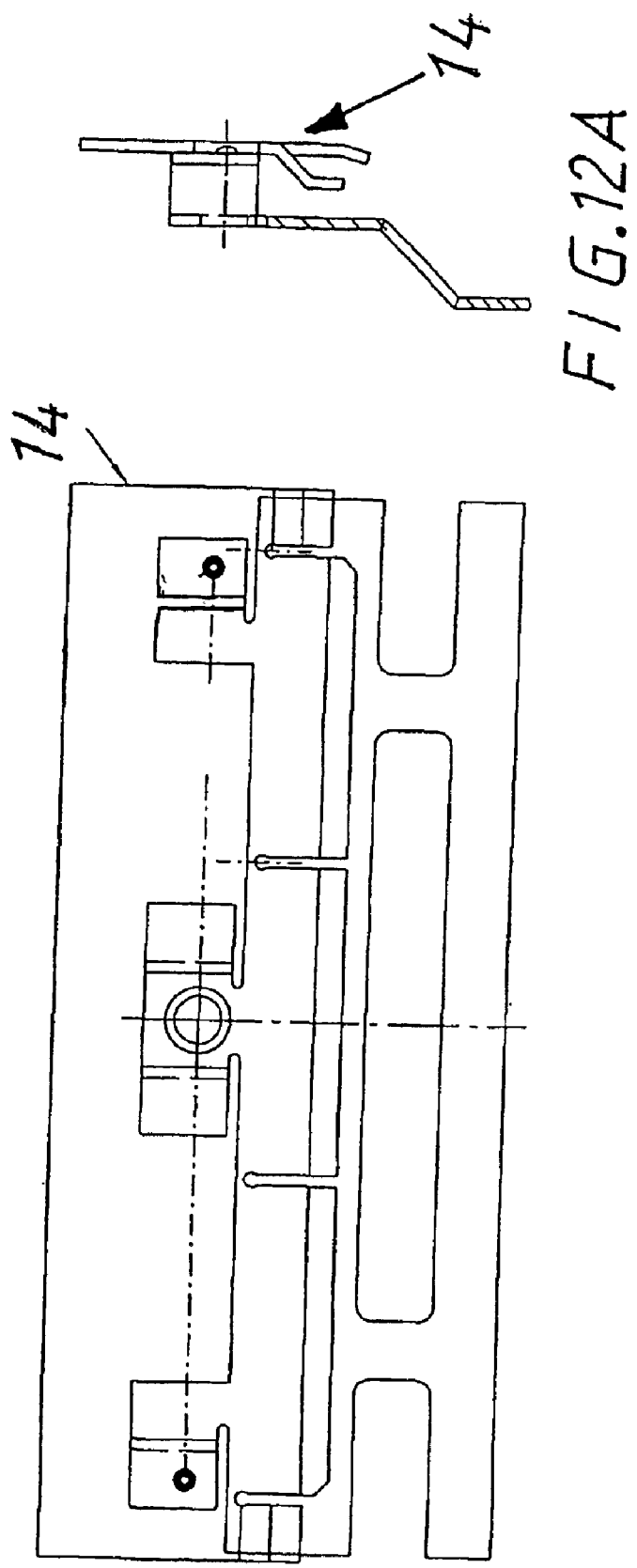

PROCESS FOR CONTROLLING THE TEMPERATURE OF A WEB AND A DEVICE TO USE FOR SAID TEMPERATURE CONTROL

PRIOR APPLICATION

This application is a U.S. national phase application based on International Application No. PCT/SE02/00826, filed 26 Apr. 2002, claiming priority from Swedish Patent Application No. 0101481-0, filed 26 Apr. 2001.

The present invention relates to a process for controlling the temperature of a product in the form of a web that is influenced by an IR ramp for surface treatment of the web.

DESCRIPTION OF THE PROBLEM

In conjunction with the manufacture of material in the form of a web, for example paper, it is difficult to guarantee the same characteristics in the web in both the longitudinal and the transverse directions. Variations in moisture content, for example, can cause the paper, after it has been cut into sheets or into quite narrow rolls, to exhibit uneven thickness and curling, and to dry at different rates and to ripple at the end user's premises. This leads to problems in copying machines or printing presses, for example. Furthermore, an uneven paper temperature during manufacturing of paper can lead to problems with calendering (when the paper is pressed between one or more rollers to achieve a better gloss), so that the gloss of the paper and its surface roughness will vary in a disadvantageous fashion. Other problems to arise are that the paper, after it has been printed in a printing press, may exhibit an uneven printing result, known as mottling. Mottling is caused by uneven distribution of the binder in the coating applied to the paper, so that the printing ink is absorbed in an irregular fashion. This leads to uniform areas of ink exhibiting an "orange peel" appearance. Among other things the method of drying the coating influences the tendency to migration by the binder with associated mottling.

Various kinds of actuators, systems, apparatuses and methods are available to correct these inconsistencies by evening out these and other variable characteristics.

A number of problems and limitations are associated with these apparatuses and methods, which are described below:

Adjustment of the Moisture Content of the Web

As far as the moisture content is concerned, this is measured either by point measurement somewhere on the web or by means of a traversing moisture sensor. Each traverse often takes between 30 and 90 seconds, after which a computer processes the information and plots an estimated moisture curve across and along the paper. The moisture sensor returns to the same point on the web in this way, for example every 60 seconds. However, since the paper is transported at speeds of up to several thousand meters per minute, the accuracy of the measurement is restricted for this reason.

The equipment used is also relatively expensive and complicated and consists of a moisture sensor (e.g. of the microwave type), a C ramp or an O ramp which holds it, a mechanism for moving the moisture sensor, a signal cable for transmitting the measurement signal to a process control computer and a computer for processing and displaying the moisture values.

Some form of "actuator" is used in order to be able to influence the moisture values that are measured in the apparatus described above. This may be a system in which water is sprayed onto those areas of the web, e.g. the paper, that are drier than desirable. It may involve injecting steam in one part of the press, so that more water is pressed from the paper. It may be an air drier divided into zones, and it may also be an IR drier, where the radiation is generated electrically or with gas which supplies more or less energy to the paper via infrared radiation, so that the moist parts are dried to a greater or less degree. An IR drier can be divided up into zones, for example 75 mm in width. Each zone is capable of steplessly varying its power by increasing or reducing the voltage over each IR element (e.g. halogen lamps), for example with the help of thyristors or semiconductor relays. Different drying can be achieved in this way, both along and across the machine.

An IR drier consists of an IR ramp positioned in a machine for the surface treatment of a web or in a paper machine. Located in the ramp as a rule is a number of IR elements or modules, so that one or more separately controlled zones are obtained. The IR ramp is often supplied with cooling air to prevent overheating of the IR ramp. The air can also be used to take up evaporated moisture or solvents.

A large number of cables (as a rule 2 for each zone) run from the IR ramp to an electrical control cubicle. If, for example, you have 90 zones, then 180 cables may be required. The electrical control cubicle may be located 50 meters from the IR ramp, for example. The cable run thus also takes up a lot of space and is associated with high costs. The electrical control cubicle contains a large number of thyristors or semiconductor relays. The effect in each zone can be varied by varying the voltage with the help of these. Electrical control cubicles are large and bulky if you need to have many zones, for example 2–15 meters wide, 2 meters tall and 0.8 meter deep. This bulky electrical control cubicle often poses a problem in conjunction with installations in existing factories, where space is limited.

By utilizing the relationship between the temperature after the IR drier and the final moisture content, as illustrated in the diagram in FIG. 1, the invention can be used to control the moisture content both across and along the machine by measuring the temperature in one or more zones across the IR ramp, and by controlling the IR power manually or automatically so that the temperature profile, and with it the moisture profile, are evened out in an appropriate fashion.

Temperature Control/Correction of the Temperature of a Web

For as long as water remains in the web, the temperature of a web exhibits a relationship with the moisture content of the web. This relationship is very strong. Briefly, it is possible to state that a lower temperature indicates a higher residual moisture content. This is illustrated in FIG. 2. What is interesting is that the point at which free water is no longer present is identified by the temperature of the web beginning to rise rapidly. This assumes that there is sufficient air circulation to enable the moist air to be transported away.

If, on the other hand, it is essentially wished to adjust the temperature of the web, it is then necessary to avoid excessive air circulation, as the effect of this would be to dry out the web and cause the temperature not to rise so greatly. There is at present no effective method for adjusting the temperature of a web-shaped material. If air is used, this causes desiccation. Air is also difficult to control in the transverse sense if it is wished to have the possibility of adjusting the temperature of the web in this direction.

IR offers one possibility, however, especially if the air circulation in the IR system is closed, so that all the air passes internally and no air passes externally. In this case, the supplied energy will essentially be used for heating.

The temperature profile of the web in the transverse direction can be of considerable importance in conjunction with calendering of the paper, since the heat of the web is transferred to the rollers in the calender. These then change their diameter and press on the paper to a greater or less degree, which influences the surface roughness, gloss and thickness.

The calender rollers are normally heated with air or induction heat in order to compensate for the uneven temperature of the web.

Improvement or Change in the Gloss and Surface Roughness of the Web

When manufacturing paper, for example, an attempt is made to change the gloss of the web and its surface roughness by causing the paper to pass through one or more nipping rollers. This increases the gloss of the paper and improves its surface roughness. It may also be wished occasionally to increase the matt characteristic of the web by the same method.

The purpose of this operation is to improve the printing characteristics. It has been found that a uniform web temperature, and also an increased web temperature, improve the result of calendering.

There are also methods whereby moisture is added to the web by spraying water or steam, which condenses on the surface to further improve the result, since a higher moisture content at the surface improves calendering (compare ironing clothes with or without moisture/steam, for example).

The apparatus described here is also intended for use for this purpose, i.e. for controlling and increasing the temperature of the web in both the transverse and the longitudinal sense. The apparatus is intended in particular to be capable of operation with its cooling air only working internally, in conjunction with which a greater increase in temperature is obtained together with reduced drying. This is easily achieved by the apparatus having replaceable or adjustable air nozzles.

The IR drier can also be combined effectively with an apparatus for spraying water or water mist onto the web, either before or after the supply of IR energy. More effective calendering is achieved in this way, as described above, because the web is made both warmer and moister. Of particular interest here is the possibility of increasing the temperature above 100 degrees C., which is not possible if you use steam to moisten and heat the web.

Minimizing Mottling

In conjunction with drying the coating, an attempt is made to dry in an optimal fashion in order to avoid mottling. The expression mottling is used to denote an uneven printing result which is particularly noticeable in darker areas of printing. This is normally done by adopting a specific drying strategy, for example by drying rapidly until the coating has reached its so-called immobilization point, i.e. the point at which free water is no longer present. It is then normally necessary to continue to dry slowly for a period, after which final drying can take place at any desired rate. It is thus important to identify the immobilization point, even if the coating and the speed of the machine change. After immobilizing the coating, the binder is no longer able to migrate. Immobilization takes place at a coating solids content of approximately 70–80%. The coating is normally dried to a final solids content of 90–95%.

Because the wet coating cannot be touched, and because it is difficult to measure the moisture content of the coating separately from that of the carrier material, e.g. paper, there is today no effective method for controlling drying so that mottling and binder migration are minimized. Moisture is normally measured only once the web is fully dried.

By contact-free measurement of the temperature in the coating, it is possible to find the point at which free water is no longer present in the web. This point is indicated by a more rapid increase in the temperature than previously with an associated increase in effect. Evaporation of free water takes place at ca. 65 degrees C. The critical point can be found manually by increasing and reducing the IR power and recording the temperature. Once a critical temperature value has been identified, it is possible to cause a regulator to control the IR power so that this temperature is then maintained. Alternatively, it is sometimes or frequently possible to let a computer program aromatically execute a short variation in the power, in conjunction with which the temperature gradient is recorded and the program varies the reference value of the temperature so that the system is running at the optimal temperature when free water is no longer present. Because the coating very often varies across the web, there is also a requirement to be able to locate the immobilization point in the transverse direction.

An arrangement previously disclosed in U.S. Pat. No. 5,236,839 A permits temperature measurement to be performed on a moving plastic web along zones in the web. The web is caused to be heated by a number of heaters, which are so arranged as to extend across the direction of movement of the web. The resulting measured temperature values are then used to indicate irregularities in the heating of the web and in an attempt to correct these. This is not easy to perform, however, due to the transverse positioning of the heaters and because it is also necessary to increase or reduce the supply of heat equally for all the heaters.

The need accordingly exists to be able to measure the temperature of an aforementioned web continuously along a specific larger surface in a safe and efficient fashion, and to be able to transmit the obtained measurement values to intended heaters so that the desired result is achieved.

The principal object of the present invention is thus, in the first instance, to solve the aforementioned problem by simple and effective means.

The aforementioned object is achieved by means of a process in accordance with the present invention, which is characterized essentially in that, with the help of a number of temperature sensors, which are situated at a mutual distance from one another laterally across the web within evenly distributed zones, the temperature is measured continuously on the web across and along its direction of movement, in that the measurement result from the respective zone of the web is transmitted to respective drier modules for subjecting the respective associated aforementioned zones of the web to heat, in that the aforementioned drier modules are supported by an aforementioned common IR ramp, closely packed together sideways across the direction of movement of the aforementioned web and extending along the direction of movement of the aforementioned web.

A further object of the invention is to identify a reliably functioning means for performing the aforementioned process with adjustable temperature monitoring.

The aforementioned further object is achieved by means of an arrangement in accordance with the invention, which is characterized essentially in that, on an IR ramp, which accommodates a number of IR lamps intended for heating and/or drying purposes contained in drier modules and extending essentially along the direction of movement of a web of the kind in question, a number of temperature sensors are arranged, at a mutual distance from one another at one end of drier modules intended to form an IR ramp and containing lamps, laterally across the web within uniformly distributed zones and are so arranged as to be situated along the web for the purpose of continuously transmitting the measured temperature in the respective zone of the web for information to a drier module for subjecting the respective associated aforementioned zones of the web to heat.

The invention is described in the following as a preferred illustrative embodiment with reference to the accompanying drawings, in which:

FIG. 1 shows a graph of the final moisture content and the web temperature after the IR drier;

FIG. 2 shows a graph of the moisture content and the web temperature and drier speed;

FIGS. 10–10C show an IR module viewed from different directions;

FIGS. 12–12A show a combined glass and lamp holder and air exhauster; and

Figure 3:
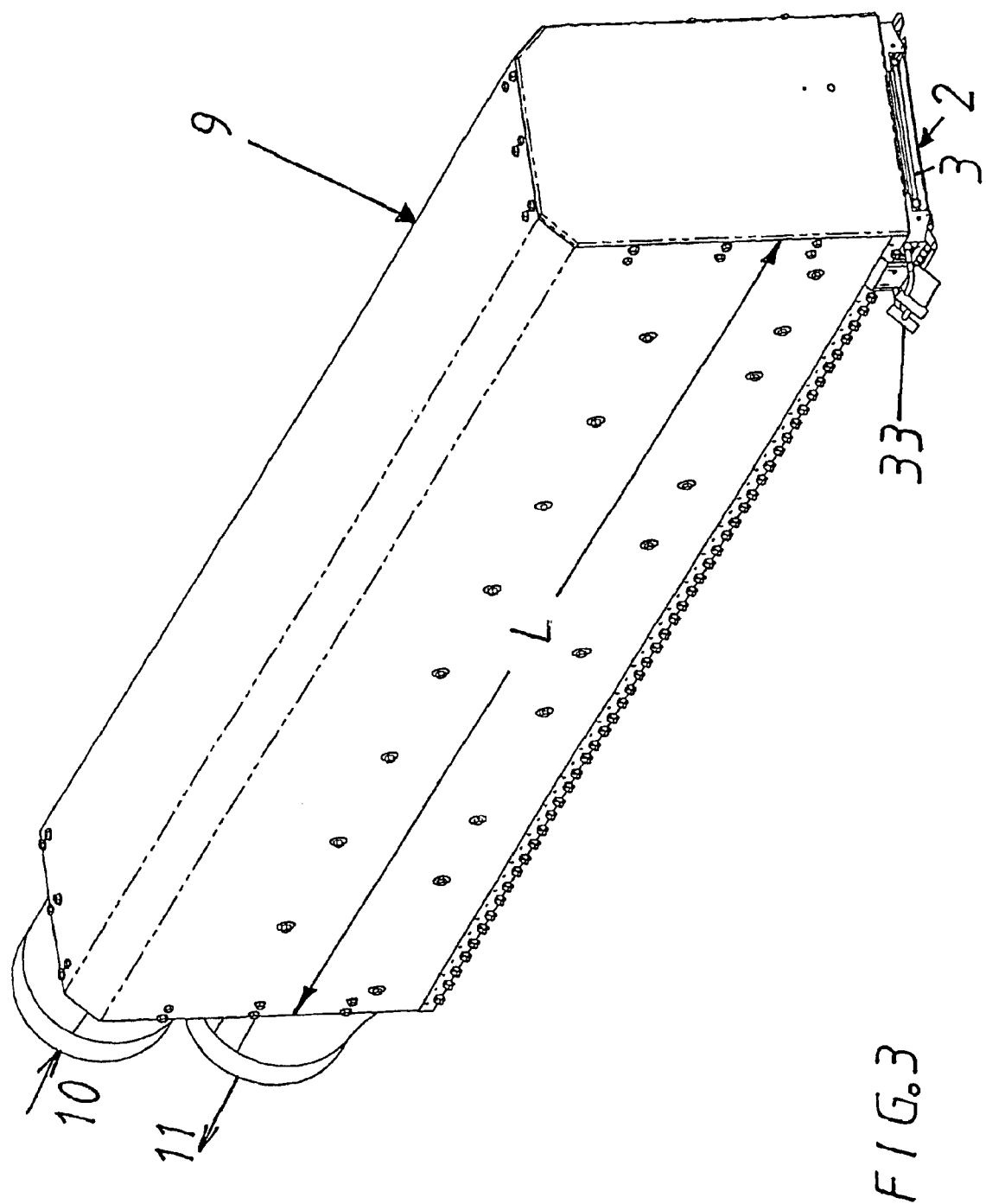
FIG. 3 shows in perspective an IR ramp for supporting a number of IR modules.
Figure 4:
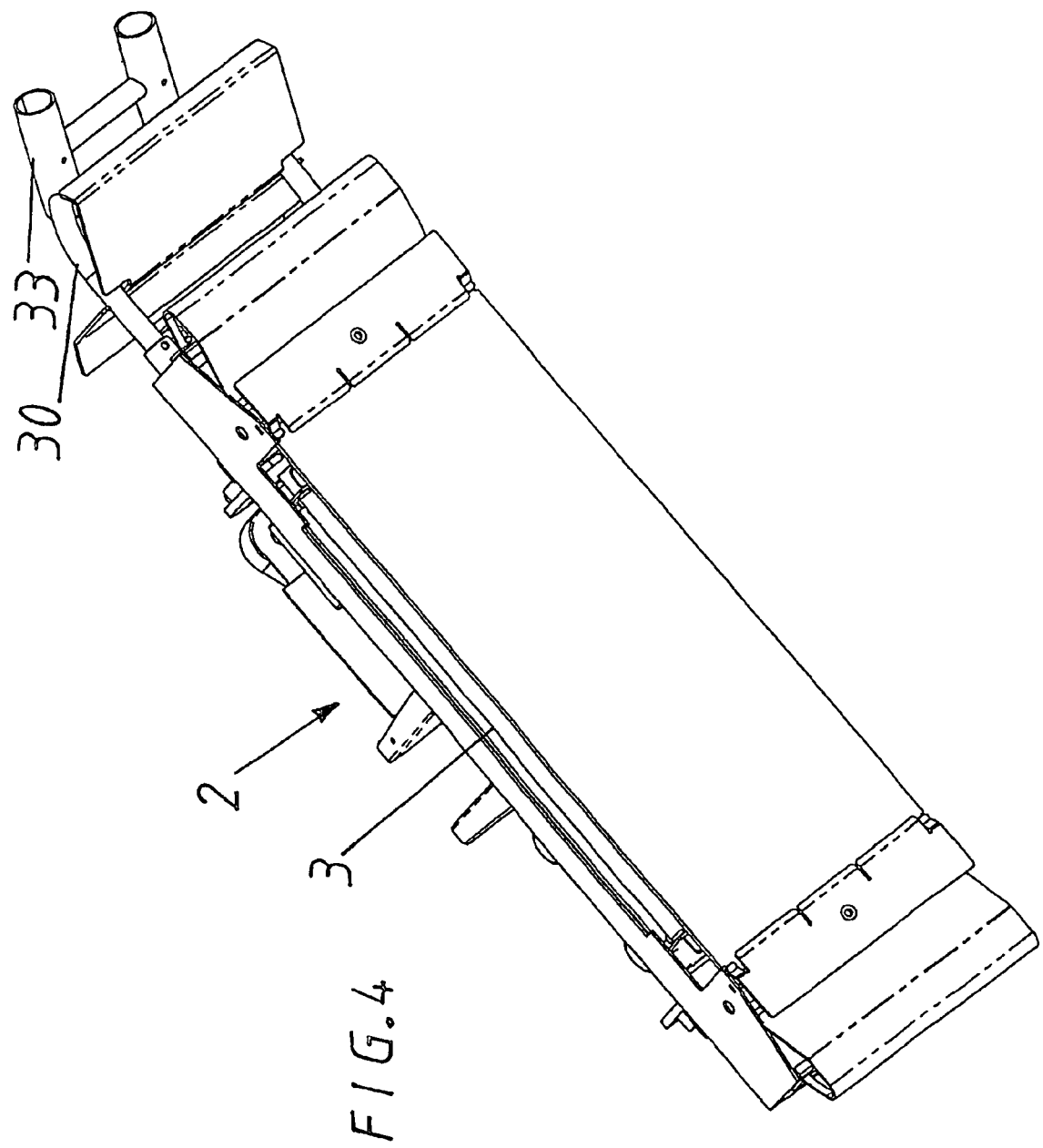
FIGS. 4–6 show an IR module viewed from different directions.
Figure 5:
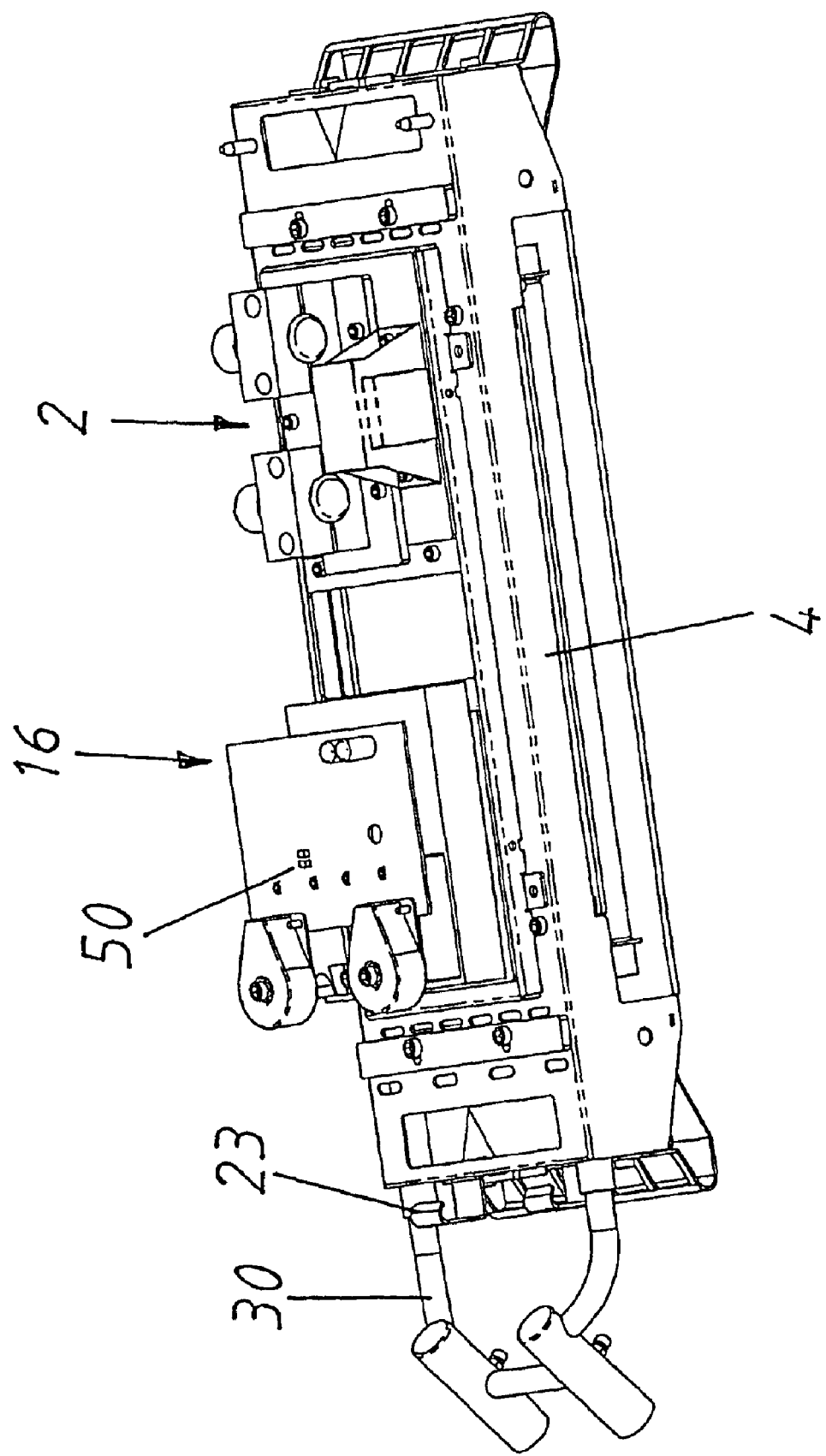
Figure 6:
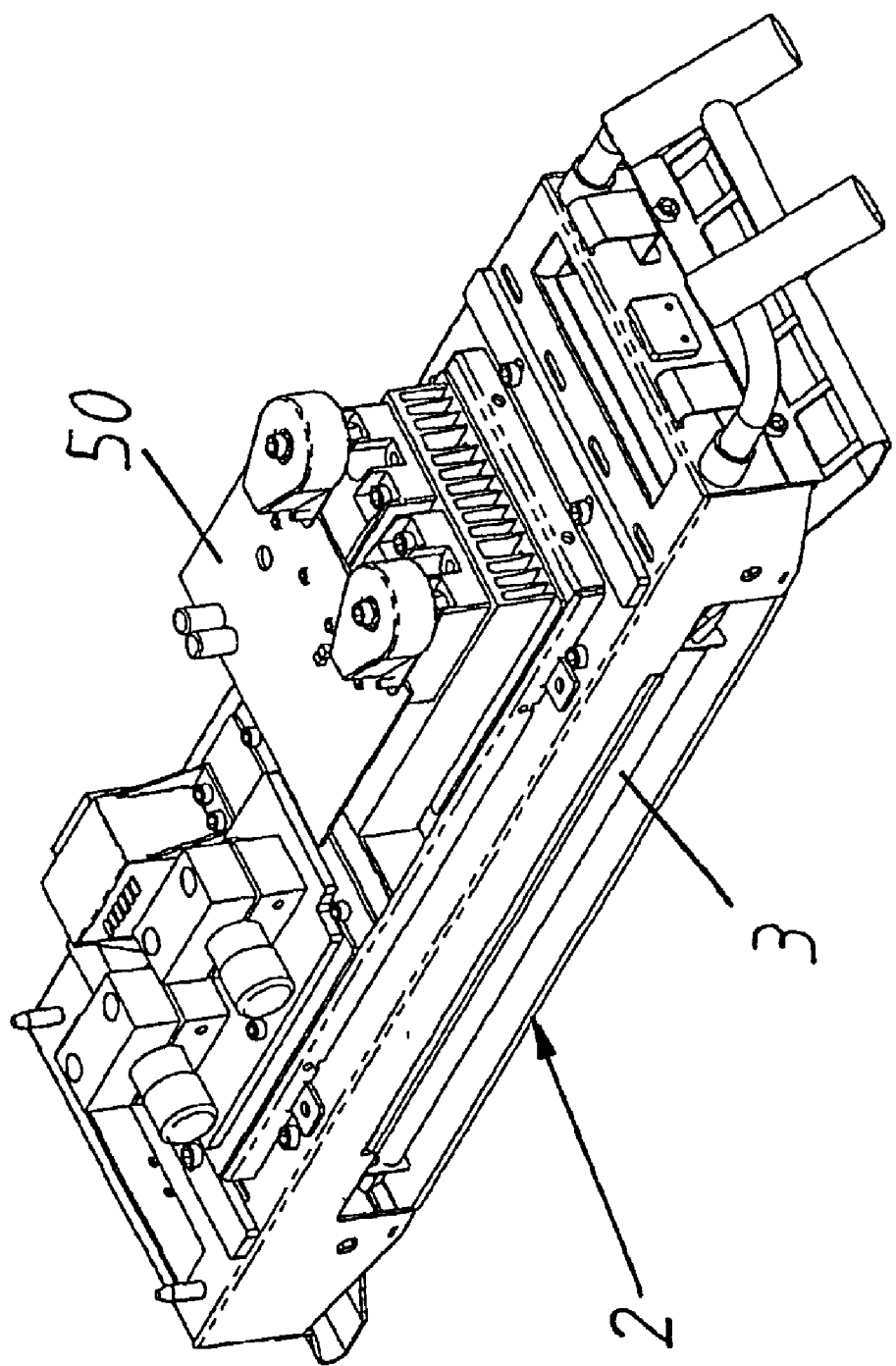
Figure 7:
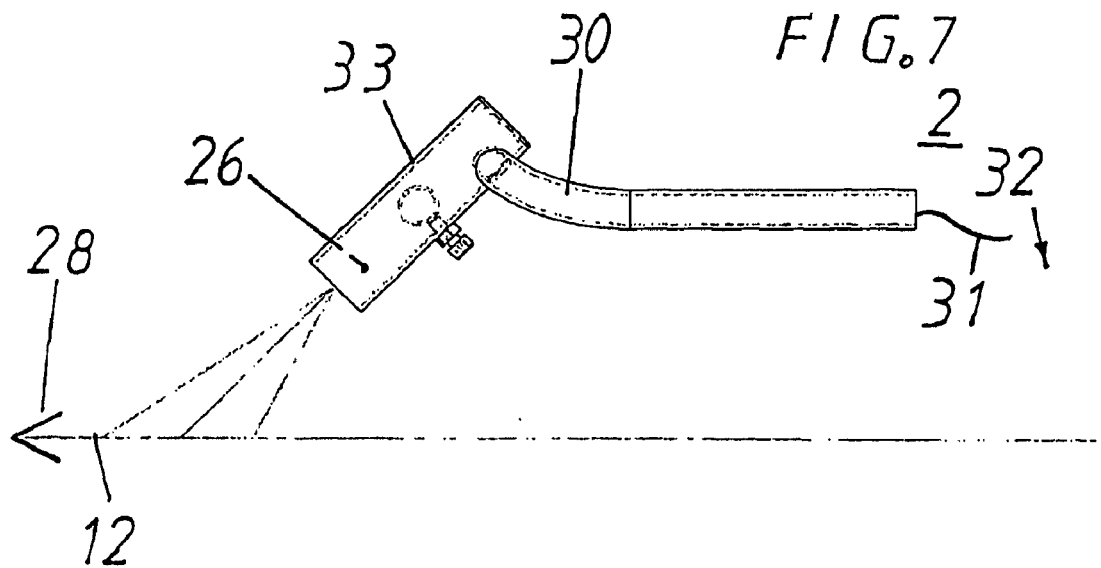
FIGS. 7–7B show one short end of an IR module and examples of temperature measuring arrangements.
Figure 7A:
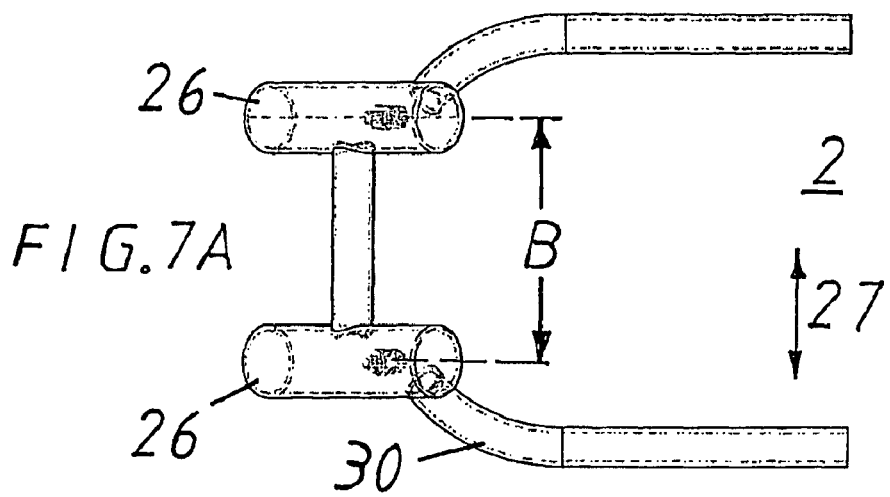
Figure 7B:
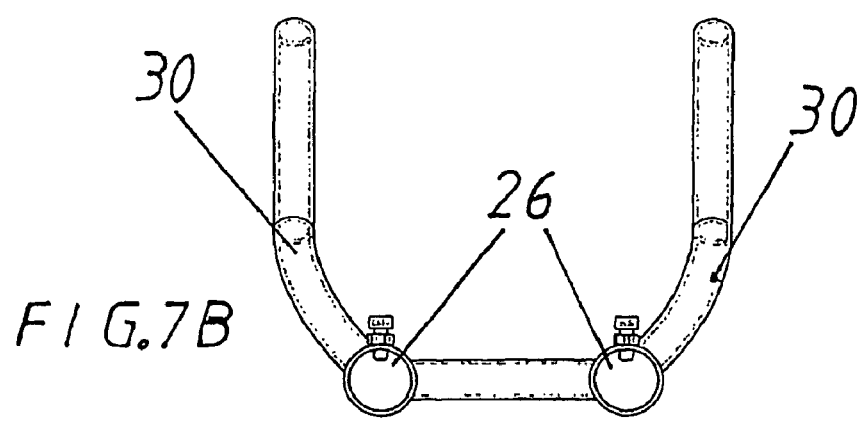
Figure 8A:
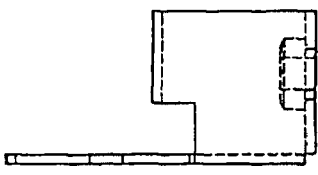
FIGS. 8–8A show IR lamp holders.
Figure 8:
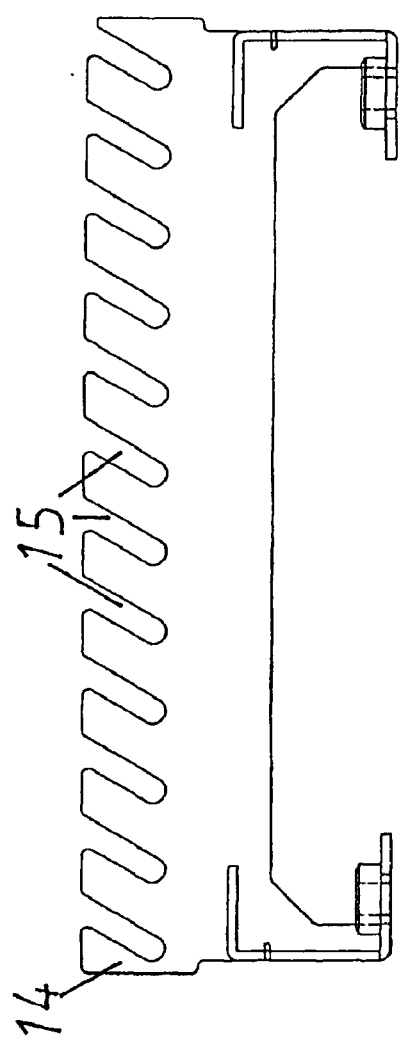
Figure 9:
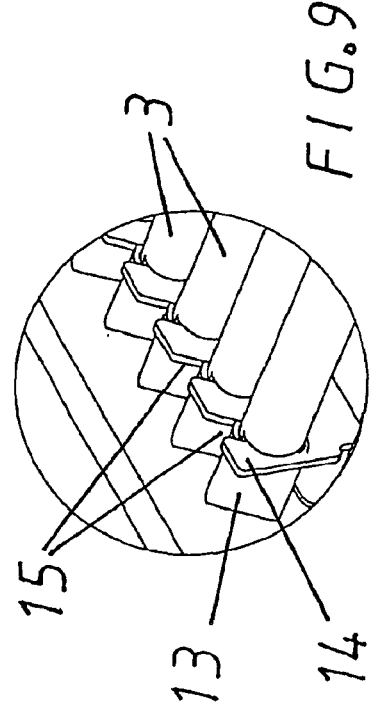
FIG. 9 shows the attachment of an IR lamp in a holder.
Figure 10C:
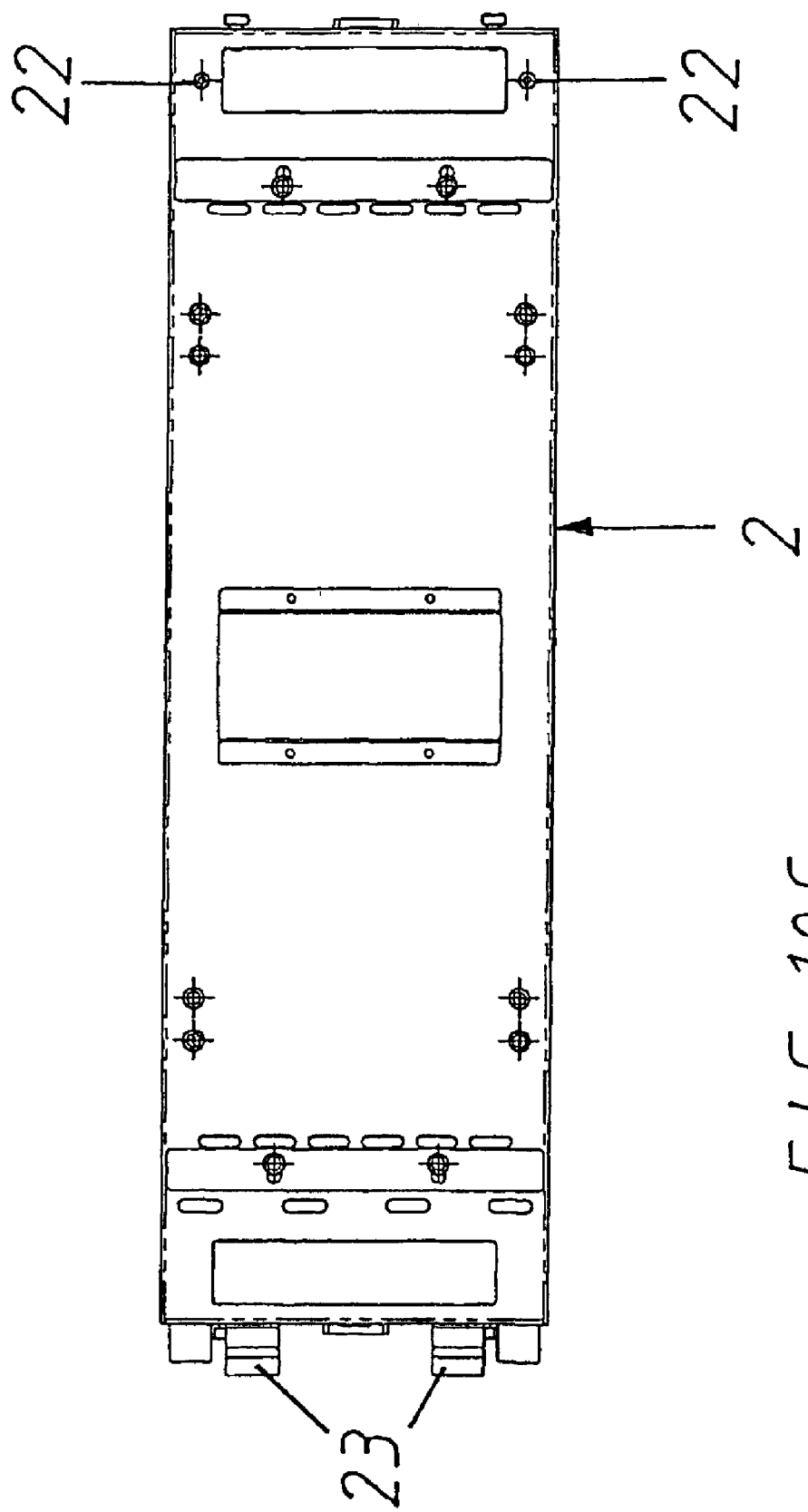
Figure 11A:
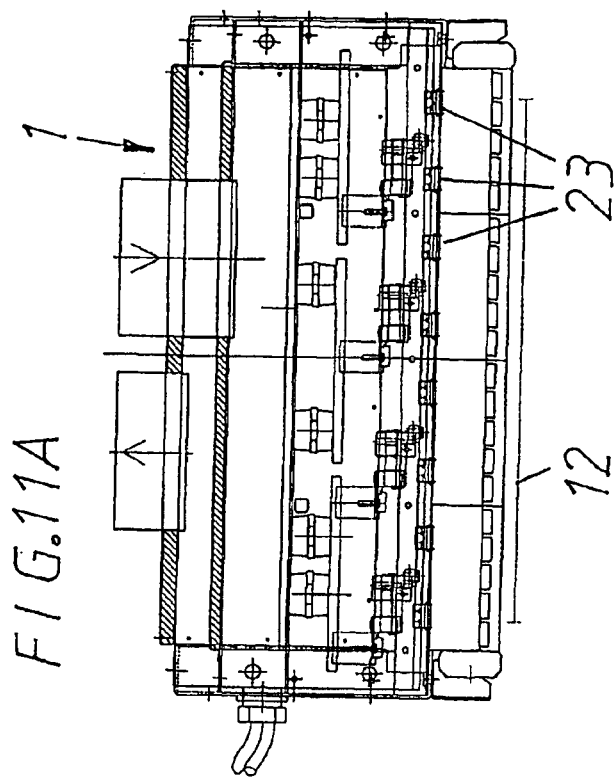
FIGS. 11–11B show an IR ramp in different views.
Figure 11:
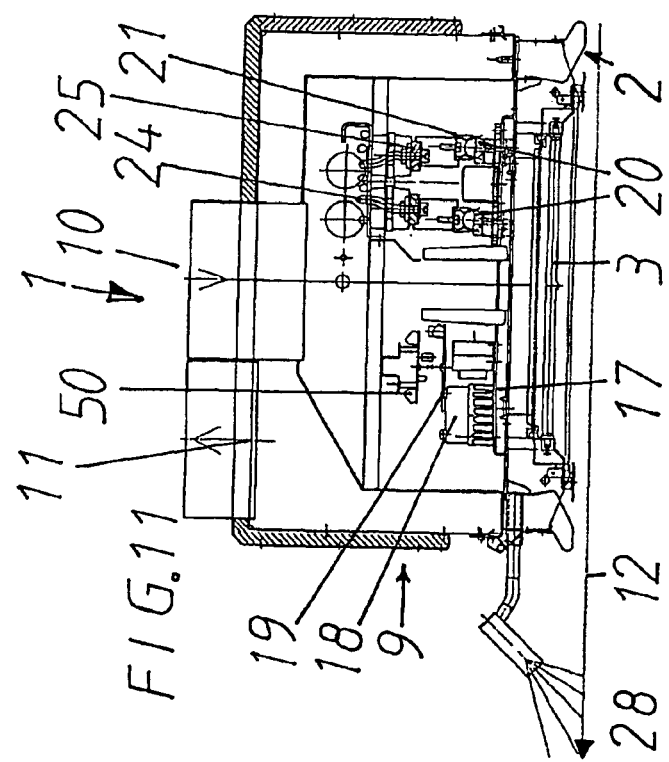
Figure 11B:
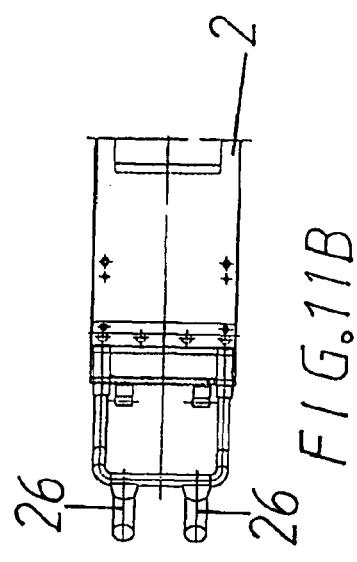
Figure 13:
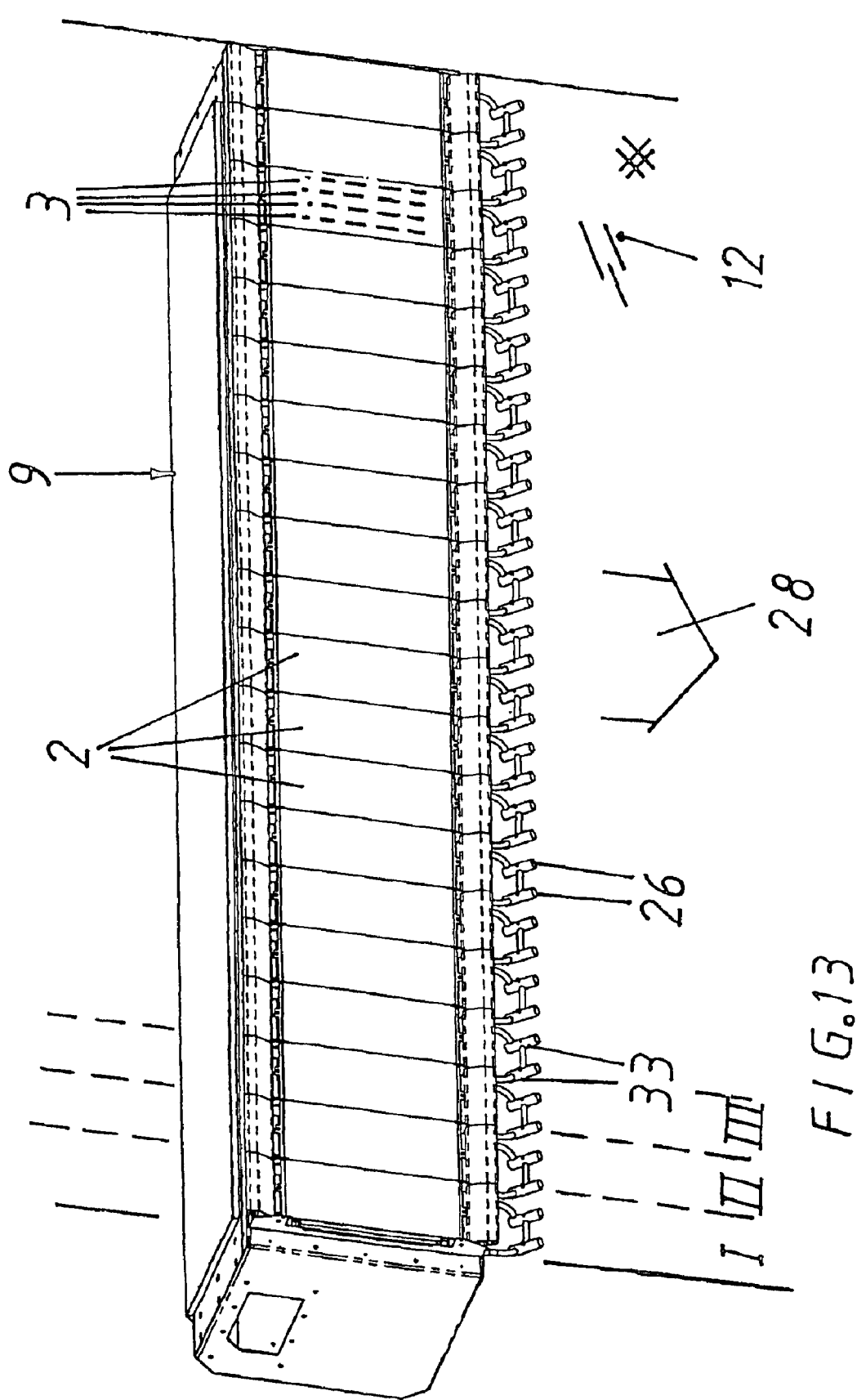
FIG. 13 shows a ramp across a web path.

The invention solves the aforementioned problems by continuous measurement of the web temperature across the web, for example in 75 mm segments (zones). Every measurement point is connected to a control device, which is capable of varying the power in the respective zone so that the temperature reference value can be achieved. Uneven temperature reference value profiles can also be reached if desired. A computer calculates what variation in power is required in order to adjust the temperature. With this method it is possible for the first time to optimize and improve binder migration and mottling across a paper machine or coater, for example, which was not previously possible in an effective manner. This can be combined with automatic searching for the optimal web temperature, where the power of the IR drier can be varied briefly and the temperature gradient checked. The invention can thus be utilized effectively and reliably on moving webs other than paper webs.
Other Problems which the Invention Proposes to Solve In conjunction with the use of IR driers to solve the above problems, these need to be able to control the power in one or more zones. In order to be able to do this, some form of electrical power control system is required. As a rule, these consist of a number of so-called thyristors or semiconductor relays installed in an electrical control cubicle. Running between the electrical control cubicle and the IR drier (drier ramp) is a number of cables, as a rule two cables per drier zone. Since there can be a large number of drier zones, there can be many cables (e.g. hundreds of cables). The electrical control cubicle itself is also voluminous and may require a space from ca. 2 m up to 10–15 m in length, with a usual width of 0.4 to 0.8 m and a height of ca. 2 m. It may be difficult to find space for this cubicle, or it may be expensive to construct a room to accommodate these cubicles. Power control cubicles are also expensive because of their size. Because certain parts of an IR drier are wearing parts (e.g. IR lamps, thyristors or semiconductor relays, fuses, etc.), fault location or replacement of these parts may be time-consuming. The invention also proposes to solve or improve these points, i.e. a smaller or eliminated power control cubicle, fewer cables and faster and simpler service and replacement of parts.
Description of IR Module with Integrated Control and Measurement The present invention is described below in detail and with reference to the accompanying drawings in accordance with FIGS. 1–12A. An electric IR drier 1 normally consists of two parts, on the one hand a number of replaceable IR modules 2, reflectors or emitters. These consist as a rule of a number of IR lamps 3 and a holder 4 made of metal and a reflector 5 behind the lamps 3. A protective glass 6 to protect the lamps 3 from dirt, usually in the form of quartz glass, electrical terminal blocks and some form of air exhaust or air nozzles 7, 8, may also be present.

The modules 2 are installed on a supporting structure or box. We can call this the ramp 9. The purpose of the ramp 9 can be to distribute supply air 10 and sometimes also exhaust air 11. The ramp 9 can consist of up to 100 modules 2, positioned close to one another side by side along the entire length L of the ramp. The modules are usually 150 m wide, but they can be both larger and smaller in width. Appropriate dimensions for the ramp are, for example, 150–10 000 mm wide, 5–700 mm high and 200–1 200 mm deep. The ramp 9 and the modules are set up so that the associated lamps 3 essentially extend along the direction of travel of the aforementioned web 12.

The invention consists of the following parts:

IR modules 2, which have one or more IR lamps 3 on their front side (facing towards a web 12 of the kind in question). The lamps 3 are installed secured at their ends 13 in a lamp holder 14. These lamp holders 14 are designed so that the ends 13 of the lamps are protected from IR radiation from the lamps 3, and that cooling air is able to flow effectively around these. The lamp ends 13 may be heated to a maximum of ca. 350° C. In order to achieve better cooling of the lamp ends 13, these are secured set at an angle. The lamps 3 are pushed securely into their holders 14 provided with slanting accommodating openings 15 in the sheet metal component 16, which at the same time is able to function as a holder for the protective glasses 6; see FIGS. 10 and 12. Situated behind these glasses 6 is a reflector 5, the purpose of which is to reflect radiation forwards. This reflector 5 can be made of a material which reflects IR radiation, for example gold-coated ceramics or steel foil. A protective glass 6 of the aforementioned kind can be positioned securely in front of the lamps 3. Also positioned on the front side are air nozzles, the purpose of which is to transport away moisture or solvents or to stabilize the web 12 in front of the IR drier 1. The air nozzles 7, 8 are appropriately replaceable so that they can be adapted depending on the circumstances. They may be open and of the "foil" type, for example. These utilize the Coanda effect to stabilize the web 12 close to the drier 1. They can also be of the overpressure type. These apply greater pressure to the web. Alternatively they may be closed. In this case the air is circulated internally in the IR ramp 2 and does not come into contact with the web 12. This gives less drying but a higher heating effect. The whole of the power controller 16 for the module 2 has been integrated on the rear side of the IR module 2.

This power controller 16 can consist of the following components: an insulated mounting plate 17. Attached to this are one or more thyristors 18 or semiconductor relays. Their task is to control the power in one or more zones steplessly. Also installed is a control card 19, which controls the thyristor or the semiconductor relays and is situated beneath a signal transfer card 50 in the module 2. This control card 19 receives control signals from a main computer or an operator's control panel. The control signal is transmitted without contact from a standard card to the control card 19, to permit simple and rapid replacement of the IR module 2 by electronics. The control card 19 also gathers information from the surroundings. The following can thus be measured: the temperature of the control card 19, and the actual power consumption, voltage and mains frequency. Feedback of the power that is actually controlled is obtained in this way. This can be used to calculate whether one or more of the lamps 3 are defective 9. It is also possible to detect faults in a thyristor/relay or in fuses.

Two fuses 20 are also installed in a readily removable fashion with the help of quick couplings, for example in the form of spring clips 21 on the rear side of the plate. Two current transformers measure the actual current.

The modules 2 are installed on their ramp 9 via quick couplings 22, 23 to enable them to be replaced quickly. The quick couplings can consist of two pins 22 on one side of the module and, for example, hook-shaped hinged quick couplings 23 at the other end of the module. When the module 2 is removed, the power supply to it is also disconnected by connecting the current via the previously mentioned fuse quick couplings 21.

The current to the modules 2 is distributed via heavy cables 24 and/or copper rails 25 which run along the ramp 2. Current is taken from these down to the aforementioned two fuses 20. The fuses 20 are necessary in order to be able to use fewer, but heavier cables 24 or copper rails 25 for the internal distribution in the ramp 9. Heavier (but fewer) cables or rails reduce the space required, which offers advantages especially in broad ramps. Integrated with the module 2 at the same time are one or more contactless temperature sensors 26. These measure the temperature of the web either before its passage through the IR drier 1 or, as shown in the drawings, after its passage through the drier. The temperature signal from each zone is transmitted to a computer, which, on the basis of this information, either can register and display the temperature profile across the web, or can automatically vary the modulation to the thyristors/semiconductor relays so that the IR power is varied as desired. A number of the previously described advantages can be achieved with this connection. The desired temperature profile after the IR drier can be set via the reference value to be entirely uniform, for example, or in accordance with some other desired profile. The temperature is measured continuously at each point. The temperature values are sent via a bus system to the main computer or the operator's control panel.

Since the IR module 2 is rapidly and simply removable for replacement with a replacement module 2, the temperature sensors 26 accompany it, which offers the possibility of subsequent simple cleaning and servicing, for example replacement of broken IR lamps or glasses, etc., without excessively lengthy production shutdowns.

The process for monitoring the temperature in the case of web-shaped products 12, which are influenced by an IR ramp 9 for the surface treatment of the web 12, thus involves the use of a number of temperature sensors 26 for the continuous measurement of the temperature of the web 12 across 27 and along its direction of movement 28 when the web is transported past the preferably fixed IR drier 1.

The temperature is appropriately measured with a number of temperature sensors 26 situated at a mutual distance B from one another laterally 27 on the IR ramp 9 within uniformly arranged zones, before or after the ramp 9 viewed in the direction of movement 28 of the web, but preferably downstream of the ramp 9.

An arrangement which lends itself appropriately to the execution of a process of the kind intended in accordance with the invention for the continuous monitoring of the temperature of web-shaped products 12, which are influenced by an IR ramp 9 for the surface treatment of the web 12, is formed by an IR ramp 9, which accommodates a number of IR lamps 3 intended for heating and/or drying purposes. A number of laterally 27 spaced temperature sensors 26 are arranged on the aforementioned ramp 9, which are so arranged as to be situated along the web 12 for the purpose of transmitting the recorded temperature of the web 12 continuously to a receiver for information.

The aforementioned temperature sensors 26 are arranged at one end of drier modules 2 provided for the purpose of forming an IR ramp 9 and containing lamps 3, which modules are detachably attached to a ramp frame extending across the intended web 12.

In accordance with the invention, at least one but preferably two temperature sensors 26 is/are accommodated by a hoop-shaped handle 30 arranged at one end of the drier module in question with an arranged wire 31 extending into the inner space 32 of the aforementioned module 2. An accommodating sleeve 33 and temperature sensor 26 can be arranged attached to the aforementioned handle 30.

The temperature transmission wire 31 extends preferably to a computer (not shown here) to permit the transmission of measurement results from the respective zone of the web 12, so that the computer is able, on the basis of this information about the temperature, to register and display the temperature profile across 27 the web and/or automatically to vary the modulation for the IR power to the web 12.

Each IR module 2 exhibits a number of attachments for securing a large number of IR lamps 3 at a time, which are arranged at an angle so that the ends 13 of the lamps 3 are so arranged as to be secured set at an angle viewed along the longitudinal median plane of the respective lamp as already described above.

Each IR ramp module 2 is so arranged as to be powered by means of a current that is conducted via cables 24 or copper rails 25 for them and is connected via fuses 20.

Each IR ramp module 2 exhibits an opening for the supply of cooling air 10 from a supply air passage running to the IR ramp 2 to the area of the attachment ends of the IR lamps, and the aforementioned air supply opening is preferably capable of connection for internal air circulation in the IR modules 2.

Each IR module 2 exhibits a hook-shaped attachment 23 for hinged attachment of the IR module at one of its ends, for example to a shaft, and guide pins 22 are accommodated at the other end of the IR module for accommodation each in its own guide hole in the ramp 9, and quick connecting devices 22, 23 of this kind are accommodated at the respective end 2A, 2B of the IR modules 2.

Simple handling, construction and function are thus achievable with the help of the invention.

The invention is naturally not restricted to the embodiment described above and illustrated in the accompanying drawings. Modifications are possible, in particular with regard to the nature of the various component parts, or by the use of equivalent technology, without departing from the area of protection afforded to the invention, as described in the patent claims.

What is claimed is:

1. Process for controlling the temperature of a product in the form of a web (12) that is influenced by an IR ramp (9) for surface treatment of the web (12) comprising:

with the help of a number of temperature sensors (26), which are situated on a common IR-ramp (9) at a mutual distance (B) from one another laterally (27) across the web (12) within evenly distributed zones (I, II, III . . . ), the temperature is measured continuously on the web (12) across (27) and along its direction of movement (28), in that the measurement result from the respective zone (I, II, III . . . ) of the web (12) is transmitted to respective drier modules (2) for subjecting the respective associated aforementioned zones (I, II, III . . . ) of the web (12) to heat, in that the aforementioned drier modules (2) are supported by an aforementioned common IR ramp (9), closely packed together sideways across the direction of movement (28) of the aforementioned web and extending along the direction of movement (28) of the aforementioned web and that the temperature is measured downstream of the ramp (9) and the lamps (3) viewed in the direction of movement (28) of the web (12);

the temperature sensors (26), disposed laterally across the common IR-ramp (9), continuously measuring the temperature of the web across the web in each respective zone;

connecting every temperature measuring point to a control device;

a computer calculating what variation in power is being required, based on temperature information continuously measured by each temperature sensor, to adjust the measured temperature to the temperature reference value in each respective zone; and varying a power sent to each respective zone to heat and adjust the measured temperature in each respective zone to a temperature reference value.

2. Process in accordance with claim 1, wherein measurement is taken at the ends of IR lamps (3) extending essentially along the direction of movement (28) of a web (12).

3. Arrangement for the execution of a process for the monitoring of the temperature of web-shaped products (12) which are influenced by an IR ramp (9) for the surface treatment of the web (12) comprising:

a process for controlling the temperature of a product in the form of a web (12) that is influenced by an IR ramp (9) for surface treatment of the web (12), with the help of a number of temperature sensors (26), which are situated on a common IR-ramp (9) at a mutual distance (B) from one another laterally (27) across the web (12) within evenly distributed zones (I, II, III . . . ), the temperature is measured continuously on the web (12), across (27) and along its direction of movement (28), in that the measurement result from the respective zone (I, II, III . . . ) of the web (12) is transmitted to respective drier modules (2) for subjecting the respective associated aforementioned zones (I, II, III . . . ) of the web (12) to heat, in that the aforementioned drier modules (2) are supported by an aforementioned common IR ramp (9), closely packed together sideways across the direction of movement (28) of the aforementioned web and extending along the direction of movement (28) of the aforementioned web and that the temperature is measured downstream of the ramp (9) and the lamps (3) viewed in the direction of movement (28) of the web (12), on a common IR ramp (9), which accommodates a number of IR lamps (3) for heating and/or drying purposes contained in drier modules (2) and extending essentially along the direction of movement (28) of a web (12), a number of temperature sensors (26) are arranged, at a mutual distance (B) from one another at one end of drier modules (2) to form an IR ramp (9) and containing lamps (3), laterally (27) across the web (12) within uniformly distributed zones (I, II, III, . . . ) and are so arranged as to be situated along the web (12) for the purpose of continuously transmitting the measured temperature in the respective zone (I, II, III . . . ) of the web (12) for information to a drier module (2) for subjecting the respective associated aforementioned zones (I, II, III . . . ) of the web (12) to heat.

4. Arrangement in accordance with claim 3 wherein the aforementioned drier modules (2) with supporting temperature sensors (26) are detachably attachable to a ramp frame extending across the intended web (12).

5. Arrangement in accordance with claim 4 wherein at least one temperature sensor (26) is accommodated by a hoop-shaped handle (30) arranged at one end of the drier module in question with a wire (31) extending into the inner space (32) of the aforementioned module.

6. Arrangement in accordance with claim 5 wherein the temperature transmission wire (31) extends to a computer to permit the transmission of measurement results from the respective zone of the web (12), and in that the computer is able, on the basis of this information about the temperature, to register and display the temperature profile across the web (12) and/or automatically to vary the modulation for the IR power to the web (12).

7. Arrangement in accordance with claim 6 wherein each IR module (2) exhibits a number of attachments (14) for IR lamps (3), which are arranged at an angle so that the ends (13) of the lamps (3) are so arranged as to be secured set at an angle viewed along the longitudinal median plane of the respective lamp.

8. Arrangement in accordance with claim 4 wherein each IR ramp module (2) is so arranged as to be powered by means of a current that is conducted via cables (24) or copper rails (25) for them and is connected via fuses (20).

9. Arrangement in accordance with claim 4 wherein each IR ramp module (2) exhibits an opening for the supply of cooling air (10) from a supply air passage running to the IR ramp (2) to the area of attachment ends (13) of the IR lamps, and in that the aforementioned air supply opening is capable of connection for internal air circulation in the IR modules (2).

10. Arrangement in accordance with claim 4 wherein each IR module (2) exhibits a hook-shaped attachment (23) for hinged attachment of the IR module (2) at one of its ends, and in that guide pins (22) are accommodated at the other end of the IR module, and in that quick connecting devices (22, 23) are accommodated at the respective end (2A, 2B) of the IR modules (2).

* * * * *